US008039704B2

(12) United States Patent
Chang et al.

(10) Patent No.: US 8,039,704 B2
(45) Date of Patent: Oct. 18, 2011

(54) NUTRITIONALLY ENHANCED INBRED MAIZE LINE HMA699ND

(75) Inventors: Ming-Tang Chang, Ames, IA (US); Anthony J. Maves, Boone, IA (US); Luiz Antonio Michelini, Ames, IA (US)

(73) Assignee: BASF Plant Science GmbH (DE)

( * ) Notice: Subject to any disclaimer, the term of this patent is extended or adjusted under 35 U.S.C. 154(b) by 391 days.

(21) Appl. No.: 12/338,285

(22) Filed: Dec. 18, 2008

(65) Prior Publication Data

US 2010/0162431 A1    Jun. 24, 2010

(51) Int. Cl.
*A01H 1/00* (2006.01)
*A01H 1/02* (2006.01)
*A01H 5/00* (2006.01)
*A01H 5/10* (2006.01)
*C12N 5/04* (2006.01)

(52) U.S. Cl. .................. 800/320.1; 800/260; 800/274; 800/275; 800/278; 800/279; 800/295; 800/298; 800/300.1; 800/301; 800/302; 800/303; 435/412; 435/424; 435/468; 435/430.1

(58) Field of Classification Search .................. None
See application file for complete search history.

(56) References Cited

U.S. PATENT DOCUMENTS

| 5,723,730 A | * | 3/1998 | Montgomery et al. | .... 800/320.1 |
| 5,773,683 A | * | 6/1998 | Foley | ............ 800/275 |

* cited by examiner

*Primary Examiner* — Medina A Ibrahim
(74) *Attorney, Agent, or Firm* — Connolly Bove Lodge & Hutz LLP

(57) ABSTRACT

An inbred maize line, designated HMA699ND, is disclosed. The invention relates to the seeds of inbred maize line HMA699ND, to the plants of inbred maize line HMA699ND and to methods for producing a maize plant, either inbred or hybrid, by crossing the inbred line HMA699ND with itself or another maize line. The invention further relates to methods for producing a maize plant containing in its genetic material one or more transgenes and to the transgenic plants produced by that method and to methods for producing other inbred maize lines derived from the inbred HMA699ND.

37 Claims, No Drawings

NUTRITIONALLY ENHANCED INBRED MAIZE LINE HMA699ND

FIELD OF THE INVENTION

This invention relates to breeding nutritionally enhanced maize, specifically relating to an inbred maize line designated HMA699ND.

BACKGROUND OF THE INVENTION

Over the last fifty years, approaches toward providing animal nutrition have changed. No longer are the animals fed whatever grain or forage may be available. Instead, the diets of animals are closely monitored for total nutrition value, and for cost. The animal on the diet is monitored, for quality and performance characteristics, and for the environmental impact of the waste from the animal. The information gathered is employed to adjust the feed to increase nutrition value of the feed and the animal performance characteristics while decreasing the cost and environmental impact.

Cereals account for about half of all feed ingredients, primarily because they are good sources of energy. Maize tends to be the preferred feed grain because of its highly digestible carbohydrate and relatively low fiber content, which is particularly important for swine and poultry (Hard, *Proc. Southwest Nutr. Conf.* 43-54 (2005)). Because of the low protein content of maize, it is common practice to use feed additives and supplements, such as protein-rich feeds, amino acids, vitamins, minerals and fats in diets for swine and poultry. The ratio of cereals to supplements has changed through the years in an attempt to maximize feeding efficiency of the animals. The feeding efficiency (the feed conversion ratio or how much feed is required to produce one pound of animal weight) is determined by the genetic potential of the animal and by the nutrients supplied to the animal. As the feed conversion ratio has risen due to genetic enhancements, the mineral and nutrient requirements for feed necessary to assure a complete and healthy diet have risen. Since an animal's ability to feed limits the amount of nutrients and calories it can consume, the feed industry has had to develop ways to make feeds that have improved protein quality (improved balance of essential amino acids), digestibility (fiber, starch, anti-nutrients), and metabolizable energy (oil).

Sources of feed protein have come under global public scrutiny in recent years because of the bovine spongiform encephalopathy, or mad cow disease, crisis associated with the feeding of meat and bone meal as the primary protein source in animal diets in many parts of the world. Plant protein sources, especially soybean meal, a residual product of the oil extraction process from soybeans relatively high in protein, have become a dominant alternative protein supplement used in feed following bans on using meat and bone meal in many parts of the world.

Plant protein sources, however, may lack sufficient levels of essential amino acids required for adequate animal health, growth and performance. Requirements vary depending on the species and age of the animal. For example, the order of the top three limiting amino acids in feed composed of corn and soybean meal is lysine, threonine, and tryptophan for swine and methionine, lysine, and threonine for poultry. (*FAO Animal Production and Health Proceedings, Protein Sources for the Animal Feed Industry*, xi-xxv, 161-183 (2004)). These limiting amino acids must be available at specific minimum levels in order for the animals to use dietary protein efficiently. (Johnson et al. "Identification of Valuable Corn Quality Traits for Livestock Feed", *Report from the Center for Crops Utilization Research*, Iowa State University, 1-22 (1999)). Crude protein in feed ingredients is not totally digestible for any species, for example corn protein is approximately 84% digestible by poultry and 82% digestible by swine (Johnson et al. (1999)). To compensate for this inefficiency, feed often contains excess protein that then results in high nitrogen excretion. More stringent environmental regulations are being imposed because high nitrogen excretion poses serious concerns to human health through ammonia or nitrate/nitrite pollution in soil and water. One solution to the problems of nitrogen pollution associated with animal feeding is to decrease crude protein in feed and supplementing feed with amino acids. A one-percentage point reduction in crude protein content in feed can yield about eight to ten percent reduction in nitrogen excretion. (*FAO Animal Production and Health Proceedings, Protein Sources for the Animal Feed Industry*, 161-183 (2004)). Supplementing of feed with amino acids can provide the required nutrients while decreasing excessive crude protein and can provide limiting amino acids when they are not sufficiently available.

Additionally, animals lack the enzymes necessary to digest the non-starch based polysaccharides present in soybean meal, and corn/soybean feed mixtures resulting in high manure volume and environmental impact. Approximately 65 to 70% of the total phosphorous in cereal grains is organically bound in phytate phosphorous, which is relatively unavailable to poultry and swine because they lack the enzyme phytase required to digest phytate, thus requiring inorganic phosphorous supplements. (Knowlton, *J. Anim. Sci.* 82 (E. Suppl.):E173-E195(2004)). The undigested phytate passes through the digestive system and leads to excretion of excess nutrients resulting in high manure volume and high levels of phosphorus in manure. Manure containing nitrogen and phosphorous at levels in excess of crop requirements results in environmental contamination especially of water resources caused by runoff. Enzymes, such as phytase, are commonly added to feed to increase digestibility. The addition of phytase can reduce the level of phosphorus released in animal waste to about half the previous level. However, the cost of phytase is about three times the cost of the conventional inorganic phosphorous supplements usually added to feed. ("Enhanced Animal Feed Will Be A Boon For The Environmental," *Economic Perspectives, Agricultural Biotechnology, An Electronic Journal of the U.S. Dept. of State*, Vol. 8, No. 3, Sep. 2003).

End-users of feed corn include livestock producer-feeders, feed manufacturers, corn millers and processors. Whether for a livestock producer-feeder who mixes and prepares their own feed or for a feed manufacturer who supplies a variety of feed products including complete ration feeds or nutrient supplements, each of the various ingredients necessary to produce the right combination of nutrients (i.e. protein, amino acids, enzymes, etc.) will need to be transported from site of production and/or processing to the site of the end-user. The availability, price, and transportation requirements and costs of each component of a particular feed will vary from year to year and in different geographical regions. Feed is usually formulated to meet nutritional requirements at a minimum dietary cost. The feed industry balances rations to supply nutrients at the least cost. Because of the variability of the supply and cost of nutrients and additives, livestock feeders and feed manufacturers would value corn traits that create substitutability for more expensive feedstuffs or additives.

Because feed is around 60% of animal production costs, any savings can be considerable, especially in large operations. Nutritionally enhanced corn which can deliver higher levels of important nutrients and metabolizable energy, and/ or enhanced digestibility and bioavailability of nutrients would provide the following benefits: reduced feed costs per unit weight gain or production of eggs or milk; reduced animal waste, particularly nitrogen and phosphorous; reduced veterinary costs and improved disease resistance; improved processing characteristics to make the feed; and improved quality (Johnson, et al. (1999)). Cost savings can be achieved by using nutritionally enhanced corn through, for example, reduced cost for needed supplements and synthetic additives, reduced transportation costs associated with the shipping of each additive and ingredients to produce the additives, reduced cost in mixing numerous additives during feed processing, and reduced costs associated with disposal of excess volume of manure.

Both traditional plant breeding and biotechnology techniques have been used to develop maize plants with desired traits such as low-phytate, high-lysine, or high-oil maize. For example, U.S. Pat. No. 5,723,730 describes an inbred corn line used to produce a hybrid with elevated percent oil and protein grain.

Examples of grain-based feed that provide improved animal nutrition and can reduce environmental impact of animal production are described by Chang et al. in U.S. Pat. Nos. 7,087,261 and 6,774,288 and in U.S. Publ. No. 2005/0246791.

There remains a need to develop inbred parental maize lines that contribute these desirable traits to the hybrids in which they are used. These traits may also include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, stalk strength, root strength, ear retention, maturity and plant and ear height, are important. Selection of germplasm that possess the desired traits is required to develop novel, desirable plant germplasm for plant breeding.

Maize is an important and valuable field crop. Thus, a continuing goal of plant breeders is to develop stable, high yielding maize hybrids that are agronomically sound. The reasons for this goal are obviously to maximize the amount of grain produced on the land used and to supply food for both animals and humans. To accomplish this goal, the corn breeder must select and develop maize plants that have the traits that result in superior parental lines for producing hybrids and that provide end-user value.

SUMMARY OF THE INVENTION

This invention provides for a novel inbred maize line designated as HMA699ND and processes for making HMA699ND. This invention relates to seed of inbred maize line HMA699ND, to the plants of inbred maize line HMA699ND, to plant parts of inbred maize line HMA699ND, and to processes for making a maize plant that comprise crossing inbred maize line HMA699ND with another maize plant. The invention also includes the maize plants produced by the seed of HMA699ND and other plants resulting from all or part of the genetics of HMA699ND and other resulting hybrids in which HMA699ND is one of the parents. In addition, this invention provides for a maize plant having the physiological and morphological characteristics of inbred HMA699ND.

This invention also provides for the tissue cultures of regenerable cells of a plant derived directly from inbred HMA699ND especially where the tissue regenerates into plants having all or essentially all of the important morphological and physiological characteristics of inbred HMA699ND. The plants regenerated from the tissue culture cells derived from inbred HMA699ND are also a part of this invention.

Inbred seed or hybrid seed produced utilizing the genetic contributions of a plant or plants derived from inbred HMA699ND are expressly included in this invention. Parts of the maize plant of the present invention are also provided, such as e.g., pollen obtained from an inbred plant and an ovule of the inbred plant.

This invention further relates to a hybrid maize seed, plant or plant part produced by crossing the inbred line HMA699ND with another maize line. This invention also relates to inbred maize lines derived from inbred maize line HMA699ND, to processes for making other inbred maize lines derived from inbred maize line HMA699ND and to the inbred maize lines and their parts derived by the use of those processes.

The invention also relates to methods for producing a maize plant containing in its genetic material one or more transgenes and to the transgenic maize plant produced by that method.

In another aspect, the present invention provides for transformed plants of HMA699ND. The transferred gene may preferably be a dominant or a recessive allele. Preferably, the transferred gene will confer such traits as herbicide resistance, insect resistance, resistance for bacterial, fungal, or viral disease, male fertility, male sterility, abiotic stress resistance/tolerance (e.g., cold tolerance, drought tolerance, etc.), enhanced nutritional quality and industrial usage. The gene may be a naturally occurring maize gene or a transgene introduced through genetic engineering techniques.

The invention further provides for developing a maize plant in a maize plant breeding program using plant breeding techniques including recurrent selection, backcrossing, pedigree breeding, restriction fragment length polymorphism enhanced selection, genetic marker enhanced selection and transformation, and haploid induction and dihaploid formation. Seed, maize plants, and parts thereof produced by such breeding methods are also part of the invention.

DEFINITIONS

In the description and tables that follow, a number of terms are used. In order to provide a clear and consistent understanding of the specification and claims, including the scope to be given such terms, the following definitions are provided:

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid F1 with one of the parental genotypes of the F1 hybrid.

Brittle Snap. This is a measure of the stalk breakage near the time of pollination, and is an indication of whether an inbred or hybrid would snap or break near the time of flowering under severe winds. Data are presented as percentage of plants that snapped.

Dropped Ears. This is a measure of the number of dropped ears per plot and represents the percentage of plants that dropped an ear prior to harvest.

% Drop Ears. Dropped Ears. This is a measure of the number of dropped ears per plot, and represents the percentage of plants that dropped an ear prior to harvest.

Ear Height. The ear height is a measure from the ground to the ear node attachment, and is measured in centimeters.

% Early Root Lodging. (See Root Lodging.) The root lodging is the percentage of plants that root lodge; i.e., those that lean from the vertical axis at an approximate 30° angle or greater would be counted as root lodged data and is collected at a earlier maturity than the % Root Lodging.

Essentially all the physiological and morphological characteristics. A plant having essentially all the physiological and morphological characteristics means a plant having the physiological and morphological characteristics as listed in Table 1 when grown in the same environmental conditions, except for the characteristics derived from a single or multiple gene conversion.

GDU Pollen. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

GDU=[(Max.+Min.)/2]−50.

The highest maximum used is 86° F. and the lowest minimum used is 50° F. For each inbred line and hybrid, it takes a certain number of GDUs to reach various stages of plant development. GDUs are a way of measuring plant maturity.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

GDU=[(Max.+Min.)/2]−50.

The highest maximum used is 86° F. and the lowest minimum used is 50° F. For each inbred line and hybrid, it takes a certain number of GDUs to reach various stages of plant development. GDUs are a way of measuring plant maturity.

GLS Rating. A 1 to 9 visual rating indicating the resistance to Gray Leaf Spot. A higher score indicates a higher resistance.

% MST=Moisture. The moisture is the actual percentage moisture of the grain at harvest.

Moisture. The moisture is the actual percentage moisture of the grain at harvest.

NLS Rating. A 1 to 9 visual rating indicating the resistance to Northern Leaf Spot. A higher score indicates a higher resistance.

% Oil. This is the percentage oil in the maize kernel as measured by NIR (near infrared spectroscopy). Oil is measured by NIR on sib-pollinated grain made by hand pollination, which controls the pollen used to make the kernels and mimics the grain that would be harvested in a whole-field setting. Oil percentage is expressed as acid hydrolysis equivalence (AHE).

Plant Height. This is a measure of the height of the hybrid from the ground to the tip of the tassel, and is measured in centimeters.

Pollen Shed. A 1 to 9 visual rating indicating the amount of pollen shed. The higher the score the more pollen shed.

% Protein. This is the percentage protein in the maize kernel as measured by NIR (near infrared spectroscopy). Protein is measured by NIR on sib-pollinated grain made by hand pollination, which controls the pollen used to make the kernels and mimics the grain that would be harvested in a whole-field setting.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Root Lodging. The root lodging is the phenotype of plants that root lodge; i.e., those that lean from the vertical axis at an approximate 30° angle or greater.

% Root Lodging. The percentage of plants that root lodge; i.e., those that lean from the vertical axis at an approximate 30° angle or greater would be counted as root lodged.

Single or Multiple Gene Converted Plant. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering (e.g., plant transformation). More than one gene can be introduced into the plant, e.g., stacked genes in a transformation event, wherein the inbred while containing the newly introduced gene or genes will still retain essentially all of the desired morphological and physiological characteristics of the inbred as listed in Table 1 when grown in the same environmental conditions.

Stalk Lodging. This is the percentage of plants that stalk lodge, i.e., stalk breakage, as measured by either natural lodging or pushing the stalks determining the percentage of plants that break off below the ear. This is a relative rating of a hybrid to other hybrids for standability.

% Starch. This is the percentage starch in the maize kernel as measured by NIR (near infrared spectroscopy). Starch is measured by NIR on sib-pollinated grain made by hand pollination, which controls the pollen used to make the kernels and mimics the grain that would be harvested in a whole-field setting.

Stay Green. Stay Green is the measure of plant health near the time of black layer formation (physiological maturity). A 1 to 9 visual rating is used, where a higher score indicates better late season plant health.

Tassel Length. Length of the tassel from the flag leaf collar to the tip of the tassel in centimeters.

Tillers. A count of the number of the tillers per plot that could possibly shed pollen was taken. Data are given as the average number of tillers per plant.

TestWt. The measure of the weight of the grain in pounds for a given volume (bushel) adjusted for 15.5 percent moisture.

Yield BU/A=Yield (Bushels/Acre). The yield in bushels/acre is the actual yield of the grain at harvest adjusted to 15.5% moisture.

Y/M. The yield divided by the percentage moisture (Y/M).

DETAILED DESCRIPTION OF THE INVENTION

Characteristics of Inbred Maize Line HMA699ND

Inbred corn line HMA699ND is a nutritionally-enhanced corn with superior characteristics, and provides an excellent parental line in crosses for producing first generation (F1) hybrid corn. Inbred corn line HMA699ND is best adapted to climates similar to the Northcentral U.S. Inbred corn line HMA699ND demonstrates good yield, above average pollen shed, good percent oil and protein content, and very good resistance to root lodging and brittle snap. Inbred corn line HMA699ND has the morphologic and physiological characteristics described in Table 1 (based primarily on data collected at Ames, Iowa).

HMA699ND was developed from the single cross TR7322/TN7765 by the doubled haploid system of plant breeding. Some of the selection criteria used in various generations include: yield, stalk quality, root quality, disease tolerance, stay green, ear retention, pollen shedding ability, and silking ability. The inbred was also evaluated as a line and in numerous crosses by research stations across the Corn Belt. The inbred has proven to have a very good combining ability in hybrid combinations.

The inbred has shown uniformity and stability. It has been self-pollinated and ear-rowed a sufficient number of generations, with careful attention to uniformity of plant type to ensure homozygosity and phenotypic stability. The line has been increased both by hand and sibbed in isolated fields with continued observations for uniformity. No variant traits have been observed or are expected in HMA699ND.

Maize Hybrids Using HMA699ND

A single cross maize hybrid results from the cross of two inbred lines, each of which has a genotype that complements the genotype of the other. The hybrid progeny of the first generation is designated F1. In the development of commercial hybrids in a maize plant breeding program, only the F1 hybrid plants are sought. F1 hybrids are more vigorous than their inbred parents. This hybrid vigor, or heterosis, can be manifested in many polygenic traits, including increased vegetative growth and increased yield.

In hybrid combination, inbred HMA699ND demonstrates good yields with average percent oil and protein content for nutritionally enhanced hybrid. The hybrids also exhibit above average resistance to Gray Leaf Spot.

HMA699ND may be used to produce hybrid maize. One such embodiment is the method of crossing inbred maize line HMA699ND with another maize plant, such as a different maize inbred line, to form a first generation F1 hybrid seed. The first generation F1 hybrid seed, plant and plant part produced by this method is an embodiment of the invention. The first generation F1 seed, plant and plant part will comprise an essentially complete set of the alleles of inbred line HMA699ND. One of ordinary skill in the art can utilize either breeder books or molecular methods to identify a particular F1 hybrid plant produced using inbred line HMA699ND. Further, one of ordinary skill in the art may also produce F1 hybrids with transgenic, male sterile and/or backcross conversions of inbred line HMA699ND.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, such as HMA699ND, which, although different from each other, breed true and are highly uniform; and (3) crossing the selected inbred lines with different inbred lines to produce the hybrids. During the inbreeding process in maize, the vigor of the lines decreases, and so one would not be likely to use HMA699ND directly to produce grain. However, vigor is restored when HMA699ND is crossed to a different inbred line to produce a commercial F1 hybrid. An important consequence of the homozygosity and homogeneity of the inbred line is that the hybrid between a defined pair of inbreds may be reproduced indefinitely as long as the homogeneity of the inbred parents is maintained.

HMA699ND may be used to produce a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C.

Breeding with Molecular Markers

Molecular markers, which includes markers identified through the use of techniques such as Isozyme Electrophoresis, Restriction Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing the inbred of the present invention. Molecular markers can be used to identify the unique genetic composition of the invention and progeny lines retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Using HMA699ND in a Breeding Program

This invention is directed to methods for producing a maize plant by crossing a first parent maize plant with a second parent maize plant wherein either the first or second parent maize plant is an inbred maize plant of the line HMA699ND. The other parent may be any other maize plant, such as another inbred line or a plant that is part of a synthetic or natural population. Any such methods using the inbred maize line HMA699ND are part of this invention: selfing, sibbing, backcrosses, recurrent selection, mass selection, pedigree breeding, double haploids, bulk selection, hybrid production, crosses to populations, and the like. These methods are well known in the art.

For example, pedigree breeding is used commonly for the improvement of self-pollinating crops or inbred lines of cross-pollinating crops. Pedigree breeding starts with the crossing of two genotypes, such as HMA699ND and one other elite inbred line having one or more desirable characteristics that is lacking or which complements HMA699ND. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The production of double haploids can also be used for the development of inbreds in the breeding program. For example, an F1 hybrid for which HMA699ND is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", *Theoretical and Applied Genetics*, 77:889 892, 1989 and U.S. patent Ser. No. 10/164,362. This can be advantageous because the process omits the generations of selfing needed to obtain a homozygous plant from a heterozygous source.

Thus, an embodiment of this invention is a process for making a substantially homozygous HMA699ND progeny plant by producing or obtaining a seed from the cross of HMA699ND and another maize plant and applying double haploid methods to the F1 seed or F1 plant or to any successive filial generation. Such methods decrease the number of generations required to produce an inbred with similar genetics or characteristics to HMA699ND.

Descriptions of breeding methods can also be found in one of several reference books (e.g., Allard, *Principles of Plant Breeding*, 1960; Simmonds, *Principles of Crop Improvement*, 1979; Fehr, "Breeding Methods for Cultivar Development", *Production and Uses*, $2^{nd}$ ed., Wilcox editor, 1987). See also U.S. Pat. No. 7,183,470 and U.S. Pat. No. 7,339,097, the disclosures of which are expressly incorporated herein by reference.

Further Embodiments of the Invention

This invention is also directed to methods for producing a maize plant by crossing a first parent maize plant with a second parent maize plant, wherein the first or second maize plant is the inbred maize plant from the line HMA699ND. Further, both first and second parent maize plants may be from the inbred line HMA699ND. Therefore, any methods using the inbred maize line HMA699ND are part of this invention: selfing, backcrosses, hybrid breeding, and crosses to populations. Any plants produced using inbred maize line HMA699ND as a parent are within the scope of this invention. Advantageously, the inbred maize line is used in crosses with other maize varieties to produce first generation (F1) maize hybrid seed and plants with superior characteristics.

As used herein, the term "plant" includes plant cells, plant protoplasts, plant cell of tissue culture from which maize plants can be regenerated, plant calli, plant clumps, and plant cells that are intact in plants or parts of plants, such as pollen, flowers, kernels, ears, cobs, leaves, husks, stalks, and the like.

Additionally, the present invention contemplates a maize plant regenerated from a tissue culture of an inbred (e.g., HMA699ND) or hybrid plant of the present invention. As is well known in the art, tissue culture of maize can be used for the in vitro regeneration of a maize plant. By way of example, a process of tissue culturing and regeneration of maize is described in European Patent Application, publication 160, 390, the disclosure of which is incorporated by reference. Maize tissue culture procedures are also described in Green and Rhodes ("Plant Regeneration in Tissue Culture of Maize," *Maize for Biological Research* (Plant Molecular Biology Association, Charlottesville, Va. 367-372 (1982)) and Duncan et al. (*Planta* 165:322-332 (1985)). The study by Duncan et al. (1985) indicates that 97% of cultured plants produced calli capable of regenerating plants. Subsequent studies have shown that both inbreds and hybrids produced 91% regenerable calli that produced plants.

Other studies indicate that non-traditional tissues are capable of producing somatic embryogenesis and plant regeneration. See Songstad et al. (*Plant Cell* Reports 7:262-265 (1988)); Rao et al. (*Maize Genetics Cooperation Newsletter*, 60:64-65 (1986)); and Conger et al. (*Plant Cell Reports*, 6:345-347 (1987)), the disclosures of which are incorporated herein by reference. Regenerable cultures may be initiated from immature embryos as described in PCT publication WO 95/06128, the disclosure of which is incorporated herein by reference.

Thus, another aspect of this invention is to provide for cells that upon growth and differentiation produce the inbred line HMA699ND.

The advent of new molecular biological techniques has allowed the isolation and characterization of genetic elements with specific functions, such as encoding specific protein products or down regulating the expression of specific endogenous genes. The genome of plants can be engineered to contain and express foreign genetic elements, or additional, or modified versions of native or endogenous genetic elements in order to alter the traits of a plant in a specific manner. Any nucleic acid sequences, whether from a different species or from the same species, which are inserted into the genome using transformation are referred to herein collectively as "transgenes". In some embodiments of the invention, a transformed variant of HMA699ND may contain one or more transgenes. Over the last fifteen to twenty years several methods for producing transgenic plants have been developed, and the present invention also relates to transformed versions of the claimed inbred maize line HMA699ND as well as hybrid combinations thereof.

Numerous methods for plant transformation including biological and physical plant transformation protocols, methods for plant cell or tissue transformation with expression vectors and in vitro culture, and methods for regeneration of plants are well known in the art, See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88; and Armstrong, "The First Decade of Maize Transformation: A Review and Future Perspective" *Maydica* 44:101 109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

One method for introducing an expression vector into plants is based on the natural transformation system of *Agrobacterium*. See, for example, Horsch et al. *Science* 227:1229 (1985). The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* mediated gene transfer are provided by Gruber et al., supra, Miki et al., supra, and Moloney et al. Plant Cell Reports 3:238(1989). See also, U.S. Pat. No. 5,591,616, issued Jan. 7, 1997.

A generally applicable method of plant transformation is Microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. See, for example, U.S. Pat. No. 5,240,855; U.S. Pat. No. 5,736,369; U.S. Pat No. 5,886,244; U.S. Pat. No. 6,258,999; U.S. Pat. No. 6,403,865; and U.S. Pat. No. 7,057,089. See also, Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, or meristematic tissue. A method of combining microprojectile bombardment with *Agrobacterium* transformation is described in U.S. Pat. No. 5,932,782, issued Aug. 3, 1999.

The most prevalent types of plant transformation involve the construction of an expression vector. Such a vector comprises a DNA sequence that contains a gene or nucleic acid sequence under the control of or operatively linked to a regulatory element, for example a promoter. The vector may contain one or more genes or nucleic acid sequences and one or more regulatory elements.

One or more genetic traits which have been engineered into the genome of a particular maize plant or plants using transformation techniques could be moved into the genome of another line using traditional breeding techniques that are well known in the plant breeding arts. For example, a backcrossing approach is commonly used to move a transgene from a transformed maize plant to an elite inbred line, and the resulting progeny would then comprise the transgene(s). In a single gene converted plant, the plant would have essentially all the desired morphological and physiological characteristics of the inbred in addition to the single gene transferred via backcrossing or via genetic engineering. Also, if an inbred line was used for the transformation then the transgenic plants could be crossed to a different inbred in order to produce a transgenic hybrid maize plant. In the same manner, more than one transgene can be transferred into the inbred.

Various genetic elements can be introduced into the plant genome using transformation. These elements include, but are not limited to genes; coding sequences; antisense nucleic acid sequences, dsRNA sequences, RNAi sequences, miRNA sequences; inducible, constitutive, and tissue specific promoters; enhancing sequences; and signal and targeting sequences, which are well known in the art.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods that are discussed, for example, by Heney and Orr, *Anal. Biochem.* 114: 92 6 (1981).

Likewise, by means of the present invention, plants can be genetically engineered to express various phenotypes of agronomic interest. Through the transformation of maize the expression of genes can be modulated to enhance disease resistance, insect resistance, herbicide resistance, agronomic, grain quality and other traits. Transformation can also be used to insert DNA sequences which control or help control male-sterility. DNA sequences native to maize as well as non-native DNA sequences can be transformed into maize and used to modulate levels of native or non-native proteins. Various promoters, targeting sequences, enhancing sequences, and other DNA sequences can be inserted into the maize genome for the purpose of modulating the expression of proteins. Reduction of the activity of specific genes (also known as gene silencing, or gene suppression) is desirable for several aspects of genetic engineering in plants.

Exemplary transgenes useful for genetic engineering of inbred maize line HMA699ND include, but are not limited to, transgenes that confer resistance/tolerance to pests (i.e. insects (such as a transgene that encodes *Bacillus thuringiensis* endotoxin), nematodes), diseases, and/or a herbicide (i.e. imidazolinone, sulfonylurea, glyphosate, glufosinate, triazine, dicamba), transgenes that confer or contribute a grain trait (i.e. modified fatty acid metabolism, decreased phytate, modified carbohydrate, improved digestibility), genes that create a site for site specific DNA integration, and genes that affect growth characteristics and/or resistance or tolerance to abiotic stress (e.g., drought and/or heat tolerance, cold tolerance, nitrogen utilization, water use efficiency). These exemplary transgenes and methods for their use in plant transformation are well known to one skilled in the art.

In a further embodiment, a method of introducing a desired trait into maize inbred line HMA699ND is provided, comprising: (a) crossing HMA699ND plants grown from HMA699ND seed, representative seed of which has been deposited under ATCC Accession No. PTA-9428, with plants of another maize line that comprise a desired trait to produce $F_1$ progeny plants; (b) selecting $F_1$ progeny plants that have the desired trait to produce selected $F_1$ progeny plants; (c) crossing the selected progeny plants with the HMA699ND plants to produce backcross progeny plants; (d) selecting for backcross progeny plants that have the desired trait and physiological and morphological characteristics of maize inbred line HMA699ND listed in Table 1 to produce selected backcross progeny plants; and (e) repeating steps (c) and (d) one or more times in succession to produce selected backcross progeny plants that comprise the desired trait and all of the physiological and morphological characteristics of maize inbred line HMA699ND listed in Table 1 when grown in the same environmental conditions. Plants produced by this method have the desired trait and all of the physiological and morphological characteristics of maize inbred line HMA699ND listed in Table 1 when grown in the same environmental conditions. Exemplary desired traits are, but are not limited to, herbicide resistance, insect resistance, disease resistance, and decreased phytate. For herbicide resistance, the resistance is conferred, for example, to an herbicide selected from the group consisting of imidazolinone, sulfonylurea, glyphosate, glufosinate, triazine, and dicamba. For insect resistance, the insect resistance is conferred, for example, by a transgene encoding a *Bacillus thuringiensis* endotoxin. Use of a transgene encoding phytase can result in decrease phytate content.

INDUSTRIAL APPLICABILITY

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. See, for example, Chang et al. in U.S. Pat. Nos. 7,087,261 and 6,774,288 and in U.S. Publ. No. 2005/0246791.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of inbred maize line HMA699ND, the plant produced from the inbred seed, the hybrid maize plant produced from the crossing of the inbred, hybrid seed, and various parts of the hybrid maize plant and transgenic versions of the foregoing, can be utilized for human food, livestock feed, and as a raw material in industry.

TABLE 1

VARIETY DESCRIPTION INFORMATION
VARIETY = HMA699ND

| | | Days | Heat Units |
|---|---|---|---|
| 1. TYPE: Nutritionally-enhanced | | | |
| 2. REGION WHERE DEVELOPED: Northcentral U.S. | | | |
| 3. MATURITY: | | | |
| | From emergence to 50% of plants in silk | 72 | 1522 |
| | From emergence to 50% of plants in pollen | 71 | 1490 |
| | Heat Units = {[Max. Temp. ($\leq$86° F.) + Min. Temp ($\geq$50° F.)] − 50}/2 | | |
| 4. PLANT: | | | |
| | Plant Height (to tassel tip) | | 231 cm |
| | Ear Height (to base of top ear) | | 93 cm |
| | Average Length of Top Ear Internode | | 14 cm |
| | Average number of Tillers | | 0 |
| | Average Number of Ears per Stalk | | 2 |
| | Anthocyanin of Brace Roots | | Faint |
| 5. LEAF: | | | |
| | Width of Ear Node Leaf | | 12 cm |
| | Length of Ear Node Leaf | | 64 cm |
| | Number of leaves above top ear | | 6 |
| | Leaf Angle from 2nd Leaf above ear at anthesis to Stalk above leaf | | 30° to 60° |
| | Leaf Color | | Medium Green - Munsell 5GY 5/6 |
| | Leaf Sheath Pubescence (Rate on scale from 1 = none to 9 = like peach fuzz) | | 3 |
| | Marginal Waves (Rate on scale from 1 = none to 9 = many) | | 4 |
| | Longitudinal Creases (Rate on scale from 1 = none to 9 = many) | | 3 |
| 6. TASSEL: | | | |
| | Number of Lateral Branches | | 7 |
| | Branch Angle from Central Spike | | Intermediate (<30° to 45°) |
| | Tassel Length (from top leaf collar to tassel top) | | 38 |
| | Pollen Shed (Rate on scale from 0 = male sterile to 9 = heavy shed) | | 7 |
| | Anther Color | | Light Green - Munsell 2.5 GY 8/8 |
| | Glume Color | | Light Green - Munsell 2.5 GY 8/6 |
| | Bar Glumes | | Absent |
| 7a. EAR: (Unhusked Data) | | | |
| | Silk Color (3 days after emergency) | | Light Green - Munsell 2.5 GY 8/4 |
| | Fresh Husk Color (25 days after 50% silking) | | Medium Green - Munsell 5GY 5/6 |
| | Dry Husk Color (65 days after 50% silking) | | Buff - Munsell 2.5Y 8/4 |
| | Position of Ear | | Upright |
| | Husk Tightness (Rate on scale from 1 = very loose to 9 = very tight) | | 6 |
| | Husk Extension | | Medium (<8 cm) |
| 7b. EAR: (Husked Ear Data) | | | |
| | Ear Length | | 14 cm |
| | Ear Diameter at mid-point | | 44 mm |
| | Ear Weight | | 98 gm |

TABLE 1-continued

VARIETY DESCRIPTION INFORMATION
VARIETY = HMA699ND

|  |  |
|---|---|
| Number of Kernel Rows | 15 |
| Kernel Rows | Distinct |
| Row Alignment | Straight |
| Shank Length | 15 cm |
| Ear Taper | Slight |
| 8. KERNEL: (Dried) |  |
| Kernel Length | 11 mm |
| Kernel Width | 9 mm |
| Kernel Thickness | 5 mm |
| Round Kernels (Shape Grade) | 49% |
| Aleurone Color Pattern | Homozygous |
| Aleurone Color | White - Munsell 2.5Y 8/2 |
| Hard Endosperm Color | Yellow - Munsell 2.5Y 7/8 |
| Endosperm Type | Normal Starch |
| Weight per 100 kernels | 23 gm |
| 9. COB: |  |
| Cob Diameter at Mid-Point | 29 mm |
| Cob Color | Red - Munsell 10R 4/6 |
| 10. AGRONOMIC TRAITS: |  |
| Stay Green (at 65 days after anthesis) (Rate on scale from 1 = worst to 9 = excellent) | 6 |
| Dropped Ears (at 65 days after anthesis) | 0% |
| Pre-anthesis Brittle Snapping | 0% |
| Pre-anthesis Root Lodging | 0% |
| Post-anthesis Root Lodging (at 65 days after anthesis) | 6% |

Hybrid Comparisons 2006

The results in Table 2A compare inbred MBS3519 crossed to inbred HMA699ND (nutritionally enhanced) and inbred LH332 crossed to inbred TN7713 (nutritionally enhanced). The results show that the MBS3519/HMA699ND hybrid produces good grain yields. The MBS3519/HMA699ND hybrid shows similar flowerings dates both GDU POLLEN and GDU SILK to the LH332/TN7713 hybrid. The MBS3519/HMA699ND hybrid has significantly better resistance to root lodging than the LH332/TN7713 hybrid. The MBS3519/HMA699ND hybrid shows average percentages for oil (% OIL) and average percentages for protein (% PROTEIN) for a nutritionally enhanced hybrid. The MBS3519/HMA699ND hybrid shows above average resistance to Gray Leaf Spot.

The results in Table 2B compare inbred MBS3519 crossed to inbred HMA699ND (nutritionally enhanced) and inbred HC33 crossed to inbred TN7713 (nutritionally enhanced). The results show that the MBS3519/HMA699ND hybrid produces good grain yields that were significantly higher than the HC33/TN7713 hybrid. The MBS3519/HMA699ND hybrid flowers significantly earlier (GDU POLLEN) than the HC33/TN7713 hybrid. The MBS3519/HMA699ND hybrid shows average percentages for oil (% OIL) and average percentages for protein (% PROTEIN) for a nutritionally enhanced hybrid. The MBS3519/TN7713 hybrid shows above average resistance to Gray Leaf Spot.

The results in Table 2C compare inbred LH332 crossed to inbred HMA699ND (nutritionally enhanced) and inbred HC33 crossed to inbred TN7713 (nutritionally enhanced). The results show that the LH332/HMA699ND hybrid produces good grain yields that were significantly higher than the HC33/TN7713 hybrid. The LH332/HMA699ND hybrid shows similar flowerings dates both GDU POLLEN and GDU SILK to the HC33/TN7713 hybrid. The LH3324/HMA699ND hybrid shows average percentages of oil (% OIL) and average percentages of protein (% PROTEIN) for a nutritionally enhanced hybrid.

The results in Table 2D compare inbred LH245 crossed to inbred HMA699ND (nutritionally enhanced) and the hybrid P34M94. The results show that the LH245/HMA699ND hybrid produces good grain yields that were not significantly different than the P34M94 hybrid. The LH245/HMA699ND hybrid shows average percentages of oil (% OIL) that were significantly higher than the P34M94 hybrid. The LH245/HMA699ND hybrid shows average percentages of protein (% PROTEIN). The LH245/HMA699ND hybrid shows above average resistance to Gray Leaf Spot.

TABLE 2A

INBREDS IN HYBRID COMBINATION REPORT 2006
VARIETY #1 = MBS3519/HMA699ND
VARIETY #2 = LH332/TN7713

|  |  | Yield BU/A | % MST | TESTWT | GDU POLLEN | GDU SILK | PLANT HEIGHT |
|---|---|---|---|---|---|---|---|
| TOTAL SUM | MBS3519/HMA699ND | 194.5 | 21.9 | 55.1 | 1355.1 | 1377.8 | 90 |
|  | LH332/TN7713 | 189.7 | 20.0 | 56.3 | 1369.0 | 1394.6 | 92 |
|  | #Compares | 19 | 19 | 18 | 5 | 5 | 4 |
|  | Difference | 4.8 | 1.9 | -1.3 | -13.9 | -16.8 | -2 |
|  | p-value | 0.33 | 0.00 | 0.00 | 0.15 | 0.19 | 0.1 |

TABLE 2A-continued

INBREDS IN HYBRID COMBINATION REPORT 2006
VARIETY #1 = MBS3519/HMA699ND
VARIETY #2 = LH332/TN7713

|  |  | EAR HEIGHT | % ROOT LODGING | % STALK LODGING | % DROP EARS | STAY GREEN | % OIL |
|---|---|---|---|---|---|---|---|
| TOTAL SUM | MBS3519/HMA699ND | 41 | 4.0 | 2.4 | 0.1 | NA | 5.9 |
|  | LH332/TN7713 | 39 | 9.2 | 2.6 | 0.0 | NA | 5.9 |
|  | #Compares | 4 | 18 | 18 | 18 | NA | 4 |
|  | Difference | 1 | −5.2 | −0.1 | 0.1 | NA | 0.1 |
|  | p-value | 0.56 | 0.00 | 0.91 | 0.20 | NA | 0.84 |

|  |  | % PROTEIN | % STARCH | GLS RATING | NLS RATING |
|---|---|---|---|---|---|
| TOTAL SUM | MBS3519/HMA699ND | 11.0 | 69.6 | 8 | NA |
|  | LH332/TN7713 | 10.4 | 69.7 | 6 | NA |
|  | #Compares | 4 | 4 | 3 | NA |
|  | Difference | 0.6 | −0.1 | 1 | NA |
|  | p-value | 0.47 | 0.86 | 0.18 | NA |

TABLE 2B

INBREDS IN HYBRID COMBINATION REPORT 2006
VARIETY #1 = MBS3519/HMA699ND
VARIETY #2 = HC33/TN7713

|  |  | Yield BU/A | % MST | TESTWT | GDU POLLEN | GDU SILK | PLANT HEIGHT |
|---|---|---|---|---|---|---|---|
| TOTAL SUM | MBS3519/HMA699ND | 194.7 | 22.0 | 55.0 | 1355.1 | 1377.8 | 90 |
|  | HC33/TN7713 | 181.3 | 20.2 | 56.1 | 1388.2 | 1402.2 | 94 |
|  | #Compares | 19 | 19 | 18 | 5 | 5 | 4 |
|  | Difference | 13.4 | 1.8 | −1.1 | −33.1 | −24.4 | −4 |
|  | p-value | 0.02 | 0.00 | 0.00 | 0.03 | 0.23 | 0.01 |

|  |  | EAR HEIGHT | % ROOT LODGING | % STALK LODGING | % DROP EARS | STAY GREEN | % OIL |
|---|---|---|---|---|---|---|---|
| TOTAL SUM | MBS3519/HMA699ND | 41 | 4.0 | 2.5 | 0.1 | NA | 5.9 |
|  | HC33/TN7713 | 39 | 6.1 | 4.6 | 0.0 | NA | 6.0 |
|  | #Compares | 4 | 18 | 18 | 18 | NA | 4 |
|  | Difference | 2 | −2.1 | −2.2 | 0.1 | NA | −0.1 |
|  | p-value | 0.4 | 0.48 | 0.15 | 0.20 | NA | 0.66 |

|  |  | % PROTEIN | % STARCH | GLS RATING | NLS RATING |
|---|---|---|---|---|---|
| TOTAL SUM | MBS3519/HMA699ND | 11.0 | 69.6 | 8 | NA |
|  | HC33/TN7713 | 10.6 | 69.4 | 6 | NA |
|  | #Compares | 4 | 4 | 3 | NA |
|  | Difference | 0.4 | 0.1 | 2 | NA |
|  | p-value | 0.68 | 0.87 | 0.3 | NA |

TABLE 2C

INBREDS IN HYBRID COMBINATION REPORT 2006
VARIETY #1 = LH332/HMA699ND
VARIETY #2 = HC33/TN7713

|  |  | Yield BU/A | % MST | TESTWT | GDU POLLEN | GDU SILK | PLANT HEIGHT |
|---|---|---|---|---|---|---|---|
| TOTAL SUM | LH332/HMA699ND | 194.2 | 21.0 | 55.6 | 1392.6 | 1419.7 | 91 |
|  | HC33/TN7713 | 181.7 | 20.2 | 56.1 | 1388.2 | 1402.2 | 94 |
|  | #Compares | 19 | 19 | 18 | 5 | 5 | 4 |
|  | Difference | 12.5 | 0.8 | −0.5 | 4.4 | 17.5 | −3 |
|  | p-value | 0.05 | 0.05 | 0.02 | 0.44 | 0.26 | 0.01 |

TABLE 2C-continued

INBREDS IN HYBRID COMBINATION REPORT 2006
VARIETY #1 = LH332/HMA699ND
VARIETY #2 = HC33/TN7713

|  |  | EAR HEIGHT | % ROOT LODGING | % STALK LODGING | % DROP EARS | STAY GREEN | % OIL |
|---|---|---|---|---|---|---|---|
| TOTAL SUM | LH332/HMA699ND | 42 | 4.5 | 2.6 | 0.0 | NA | 6.0 |
|  | HC33/TN7713 | 39 | 6.0 | 4.8 | 0.0 | NA | 6.0 |
|  | #Compares | 4 | 18 | 18 | 18 | NA | 4 |
|  | Difference | 3 | −1.5 | −2.2 | 0.0 | NA | 0.0 |
|  | p-value | 0.01 | 0.62 | 0.13 | 1.00 | NA | 0.88 |

|  |  | % PROTEIN | % STARCH | GLS RATING | NLS RATING |
|---|---|---|---|---|---|
| TOTAL SUM | LH332/HMA699ND | 10.7 | 69.8 | 7 | NA |
|  | HC33/TN7713 | 10.6 | 69.4 | 6 | NA |
|  | #Compares | 4 | 4 | 3 | NA |
|  | Difference | 0.1 | 0.3 | 1 | NA |
|  | p-value | 0.89 | 0.42 | 0.42 | NA |

TABLE 2D

INBREDS IN HYBRID COMBINATION REPORT 2006
VARIETY #1 = LH245/HMA699ND
VARIETY #2 = P34M94

|  |  | Yield BU/A | % MST | TESTWT | GDU POLLEN | GDU SILK | PLANT HEIGHT |
|---|---|---|---|---|---|---|---|
| TOTAL SUM | LH245/HMA699ND | 195.2 | 23.6 | 54.5 | 1389.5 | 1418.9 | 93 |
|  | P34M94 | 198.8 | 19.5 | 56.5 | 1385.6 | 1388.2 | 88 |
|  | #Compares | 19 | 19 | 18 | 5 | 5 | 4 |
|  | Difference | −3.5 | 4.1 | −2.0 | 3.9 | 30.7 | 4 |
|  | p-value | 0.17 | 0.00 | 0.00 | 0.72 | 0.01 | 0.02 |

|  |  | EAR HEIGHT | % ROOT LODGING | % STALK LODGING | % DROP EARS | STAY GREEN | % OIL |
|---|---|---|---|---|---|---|---|
| TOTAL SUM | LH245/HMA699M | 42 | 2.5 | 1.4 | 0.1 | NA | 5.2 |
|  | P34M94 | 37 | 4.7 | 2.0 | 0.0 | NA | 4.7 |
|  | #Compares | 4 | 18 | 18 | 18 | NA | 4 |
|  | Difference | 5 | −2.3 | −0.6 | 0.1 | NA | 0.5 |
|  | p-value | 0.23 | 0.11 | 0.38 | 0.47 | NA | 0.03 |

|  |  | % PROTEIN | % STARCH | GLS RATING | NLS RATING |
|---|---|---|---|---|---|
| TOTAL SUM | LH245/HMA699ND | 10.7 | 70.5 | 8 | NA |
|  | P34M94 | 11.0 | 70.7 | 8 | NA |
|  | #Compares | 4 | 4 | 3 | NA |
|  | Difference | −0.4 | −0.2 | 0 | NA |
|  | p-value | 0.50 | 0.27 | 0.42 | NA |

Hybrid Comparisons 2007

The results in Table 3A compare inbred SG1890HX1.1 crossed to inbred HMA699ND (nutritionally enhanced) and inbred LH2455BT1.1 crossed to inbred TN7713 (nutritionally enhanced). The results show that the SG1890HX1.1 hybrid produces good grain yields. The SG1890HX1.1/HMA699ND hybrid shows significantly lower moisture percentages (% MST) than the LH245BT1.1/TN7713 hybrid. The SG1890HX1.1 hybrid shows similar flowerings dates both GDU POLLEN and GDU SILK to the LH245ST1.1/TN7713 hybrid. The SG1890HX1.1/HMA699ND hybrid has significantly lower percentages of root lodging than the LH245BT1.1/TN7713 hybrid. The SG1890HX1.1/HMA699ND) hybrid shows average percentages of oil (% OIL) that were significantly higher than the LH245BT1.1/TN7713 hybrid. The SG1890HX1.1/HMA699ND hybrid shows above average resistance to Gray Leaf Spot.

The results in Table 3B compare inbred LH332BT1.1 crossed to inbred HMA699ND (nutritionally enhanced) and inbred LH245BT1.1 crossed to inbred TN7713 (nutritionally enhanced). The results show that the LH332BT1.1/HMA699ND hybrid produces good grain yields. The LH332BT1.1/HMA699ND hybrid shows significantly lower moisture percentages (% MST) than the LH245BT1.1/TN7713 hybrid. The LH332BT1.1/HMA699ND hybrid shows average percentages of oil (% OIL) that were significantly higher than the LH245BT1.1/TN7713 hybrid. The LH332BT1.1/HMA699ND hybrid shows average percentages of protein (% PROTEIN) for a nutritionally enhanced hybrid. The LH332BT1.1/HMA699ND hybrid shows above average resistance to Gray Leaf Spot.

The results in Table 3C compare inbred MBS3519 crossed to inbred HMA699ND (nutritionally enhanced) and inbred TR7476 crossed to inbred TN7713 (nutritionally enhanced). The results show that the MBS3519/HMA699ND hybrid produces significantly higher grain yields and significantly lower moisture percentages (% MST) than the TR7476/TN7713 hybrid. The MBS3519/HMA699ND hybrid shows similar flowerings dates both GDU POLLEN and GDU SILK to the TR7476/TN7713 hybrid. The MBS3519/HMA699ND hybrid has significantly lower stalk lodging percentages than the TR7476/TN7713 hybrid. The MBS3519/HMA699ND hybrid shows average percentages of oil (% OIL) and percentages of protein (% PROTEIN) for a nutritionally enhanced hybrid. The MBS3519/HMA699ND hybrid shows above average resistance to Gray Leaf Spot.

The results in Table 3D compare inbred LH311 crossed to inbred HMA699ND (nutritionally enhanced) and inbred TR7476 crossed to TN7713 (nutritionally enhanced). The results show that the LH311/HMA699ND hybrid produces good grain yields. The LH311/HMA699ND hybrid shows similar flowerings dates both GDU POLLEN and GDU SILK to the TR7476/TN7713 hybrid. The LH311/HMA699ND hybrid shows above average percentages of oil (% OIL) that were significantly higher than the TR7476/TN7713 hybrid. The LH311/HMA699ND hybrid shows above average resistance to Gray Leaf Spot.

TABLE 3A

INBREDS IN HYBRID COMBINATION REPORT 2007
VARIETY #1 = SGI890HX1.1/HMA699ND
VARIETY #2 = LH245BT1.1/TN7713

|  |  | Yield BU/A | % MST | TESTWT | GDU POLLEN | GDU SILK | PLANT HEIGHT |
|---|---|---|---|---|---|---|---|
| TOTAL SUM | SGI890HX1.1/HMA699ND | 190.7 | 18.7 | 56.4 | 1459.0 | 1465.3 | 99 |
|  | LH245BT1.1/TN7713 | 192.9 | 19.4 | 56.4 | 1440.9 | 1450.3 | 98 |
|  | #Compares | 28 | 28 | 22 | 4 | 4 | 8 |
|  | Difference | -2.2 | -0.7 | 0.0 | 18.1 | 15.0 | 1 |
|  | p-value | 0.63 | 0.01 | 0.93 | 0.19 | 0.14 | 0.36 |

|  |  | EAR HEIGHT | % ROOT LODGING | % STALK LODGING | % DROP EARS | STAY GREEN | % OIL |
|---|---|---|---|---|---|---|---|
| TOTAL SUM | SGI890HX1.1/HMA699ND | 47 | 0.5 | 1.1 | 0.0 | 6 | 5.9 |
|  | LH245BT1.1/TN7713 | 43 | 3.7 | 1.2 | 0.0 | 4 | 5.5 |
|  | #Compares | 8 | 27 | 27 | 22 | 3 | 3 |
|  | Difference | 4 | -3.2 | -0.1 | 0.0 | 2 | 0.4 |
|  | p-value | 0.01 | 0.05 | 0.90 | 1.00 | 0.37 | 0.01 |

|  |  | % PROTEIN | % STARCH | GLS RATING | NLS RATING |
|---|---|---|---|---|---|
| TOTAL SUM | SGI890HX1.1/HMA699ND | 9.2 | 70.6 | 7 | 8 |
|  | LH245BT1.1/TN7713 | 10.6 | 70.0 | 6 | 7 |
|  | #Compares | 3 | 3 | 4 | 1 |
|  | Difference | -1.4 | 0.6 | 1 | 1 |
|  | p-value | 0.13 | 0.28 | 0.25 | NA |

TABLE 3B

INBREDS IN HYBRID COMBINATION REPORT 2007
VARIETY #1 = LH332BT1.1/HMA699ND
VARIETY #2 = LH245BT1.1/TN7713

|  |  | Yield BU/A | % MST | TESTWT | GDU POLLEN | GDU SILK | PLAN HEIGHT |
|---|---|---|---|---|---|---|---|
| TOTAL SUM | LH332BT1.1/HMA699ND | 199.4 | 18.1 | 57.1 | 1421.3 | 1446.8 | 99 |
|  | LH245BT1.1/TN7713 | 195.0 | 20.0 | 56.2 | 1409.8 | 1428.8 | 95 |
|  | #Compares | 30 | 30 | 27 | 4 | 4 | 6 |
|  | Difference | 4.3 | -2.0 | 0.8 | 11.5 | 18.0 | 4 |
|  | p-value | 0.45 | 0.00 | 0.00 | 0.68 | 0.19 | 0.32 |

|  |  | EAR HEIGHT | % ROOT LODGING | % STALK LODGING | % DROP EARS | STAY GREEN | % OIL |
|---|---|---|---|---|---|---|---|
| TOTAL SUM | LH332BT1.1/HMA699ND | 47 | 4.3 | 1.1 | 0.0 | 7 | 5.7 |
|  | LH245BT1.1/TN7713 | 41 | 7.0 | 3.3 | 0.1 | 4 | 5.4 |
|  | #Compares | 6 | 28 | 28 | 21 | 3 | 3 |
|  | Difference | 6 | -2.7 | -2.2 | -0.1 | 3 | 0.3 |
|  | p-value | 0.02 | 0.43 | 0.18 | 0.33 | 1 | 0.04 |

TABLE 3B-continued

INBREDS IN HYBRID COMBINATION REPORT 2007
VARIETY #1 = LH332BT1.1/HMA699ND
VARIETY #2 = LH245BT1.1/TN7713

|  |  | % PROTEIN | % STARCH | GLS RATING | NLS RATING |
|---|---|---|---|---|---|
| TOTAL SUM | LH332BT1.1/HMA699ND | 10.8 | 69.7 | 7 | 7 |
|  | LH245BT1.1/TN7713 | 10.5 | 70.1 | 6 | 8 |
|  | #Compares | 3 | 3 | 3 | 1 |
|  | Difference | 0.3 | −0.4 | 1 | −1 |
|  | p-value | 0.43 | 0.48 | 0.48 | NA |

TABLE 3C

INBREDS IN HYBRID COMBINATION REPORT 2007
VARIETY #1 = MBS3519/HMA699ND
VARIETY #2 = TR7476/TN7713

|  |  | Yield BU/A | % MST | TESTWT | GDU POLLEN | GDU SILK | PLANT HEIGHT |
|---|---|---|---|---|---|---|---|
| TOTAL SUM | MBS3519/HMA699ND | 201.7 | 18.5 | 56.9 | 1389.5 | 1408.3 | 91 |
|  | TR7476/TN7713 | 191.6 | 19.2 | 56.8 | 1416.3 | 1440.3 | 99 |
|  | #Compares | 31 | 31 | 28 | 4 | 4 | 6 |
|  | Difference | 10.0 | −0.7 | 0.1 | −26.8 | −32.0 | −7 |
|  | p-value | 0.02 | 0.02 | 0.66 | 0.47 | 0.25 | 0.02 |

|  |  | EAR HEIGHT | % ROOT LODGING | % STALK LODGING | % DROP EARS | STAY GREEN | % OIL |
|---|---|---|---|---|---|---|---|
| TOTAL SUM | LH332BT1.1/HMA699ND | 41 | 0.7 | 0.9 | 0.0 | 5 | 5.8 |
|  | P33B51 | 43 | 2.2 | 2.4 | 0.0 | 4 | 5.6 |
|  | #Compares | 6 | 29 | 29 | 23 | 3 | 3 |
|  | Difference | −2 | −1.5 | −1.6 | 0.0 | 1 | 0.3 |
|  | p-value | 0.44 | 0.16 | 0.04 | 1.00 | 0.18 | 0.21 |

|  |  | % PROTEIN | % STARCH | GLS RATING | NLS RATING |
|---|---|---|---|---|---|
| TOTAL SUM | LH332BT1.1/HMA699ND | 10.1 | 70.0 | 7 | 8 |
|  | P33B51 | 9.4 | 71.1 | 7 | 7 |
|  | #Compares | 3 | 3 | 3 | 1 |
|  | Difference | 0.7 | −1.1 | 0 | 1 |
|  | p-value | 0.33 | 0.10 | 0.42 | NA |

TABLE 3D

INBREDS IN HYBRID COMBINATION REPORT 2007
VARIETY #1 = LH311/HMA699ND
VARIETY #2 = TR7476/TN7713

|  |  | Yield BU/A | % MST | TESTWT | GDU POLLEN | GDU SILK | PLANT HEIGHT |
|---|---|---|---|---|---|---|---|
| TOTAL SUM | LH311/HMA699ND | 196.9 | 20.2 | 55.5 | 1493.7 | 1493.7 | 98 |
|  | TR7476/TN7713 | 190.6 | 18.9 | 56.1 | 1478.3 | 1466.0 | 101 |
|  | #Compares | 18 | 18 | 15 | 3 | 3 | 3 |
|  | Difference | 6.3 | 1.4 | −0.6 | 15.3 | 27.7 | −2 |
|  | p-value | 0.31 | 0.00 | 0.00 | 0.42 | 0.24 | 0.34 |

|  |  | EAR HEIGHT | % ROOT LODGING | % STALK LODGING | % DROP EARS | STAY GREEN | % OIL |
|---|---|---|---|---|---|---|---|
| TOTAL SUM | LH311/HMA699ND | 49 | 2.3 | 2.3 | 0.0 | 7 | 6.0 |
|  | TR7476/TN7713 | 47 | 7.2 | 3.3 | 0.0 | 3 | 5.4 |
|  | #Compares | 3 | 17 | 17 | 17 | 1 | 3 |
|  | Difference | 2 | −4.9 | −1.0 | 0.0 | 4 | 0.6 |
|  | p-value | 0.23 | 0.13 | 0.58 | 1.00 | NA | 0.01 |

TABLE 3D-continued

INBREDS IN HYBRID COMBINATION REPORT 2007
VARIETY #1 = LH311/HMA699ND
VARIETY #2 = TR7476/TN7713

| | | % PROTEIN | % STARCH | GLS RATING | NLS RATING |
|---|---|---|---|---|---|
| TOTAL SUM | LH311/HMA699ND | 9.9 | 70.2 | 8 | NA |
| | TR7476/TN7713 | 9.2 | 71.4 | 6 | NA |
| | #Compares | 3 | 3 | 2 | NA |
| | Difference | 0.7 | −1.2 | 2 | NA |
| | p-value | 0.37 | 0.14 | 1 | NA |

DEPOSIT INFORMATION

Inbred seeds of HMA699ND have been placed on deposit with the American Type Culture Collection (ATCC), Manassas, Va., under Deposit Accession Number PTA-9428 on Aug. 26, 2008. The seed were tested on Sep. 8, 2008 and were viable. Access to this deposit will be available during the pendency of the application to the Commissioner of Patents and Trademarks and persons determined by the Commissioner to be entitled thereto upon request. Upon granting of an claims in the application, the Applicants will make the deposit available to the public pursuant to 37 CFR 1.808. The deposit will be maintained in the ATCC Depository, which is a public depository, for a period of 30 years, or 5 years after the most recent request, or for the enforceable life of the patent, whichever is longer, and will be replaced if it becomes nonviable during that period. Applicants have no authority to waive any restrictions imposed by law on the transfer of biological material or its transportation in commerce. Applicants do not wave any infringement of their rights granted under this patent.

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Seed of maize inbred line designated HMA699ND, representative seed of said line having been deposited under ATCC Accession No. PTA-9428.

2. A maize plant, or a part thereof, produced by growing the seed of claim 1.

3. Pollen of the plant of claim 2.

4. An ovule of the plant of claim 2.

5. The maize plant of claim 2 wherein said plant has been detasseled or is male sterile.

6. A tissue culture of regenerable cells produced from the plant of claim 2.

7. The tissue culture of claim 6, wherein cells of the tissue culture are from a tissue selected from the group consisting of leaf, pollen, embryo, root, root tip, anther, silk, flower, kernel, ear, cob, husk, and stalk.

8. A protoplast produced from the tissue culture of claim 6.

9. A maize plant regenerated from the tissue culture of claim 6, wherein the regenerated plant has all the morphological and physiological characteristics of inbred line HMA699ND, representative seed of said line having been deposited under ATCC Accession No. PTA-9428.

10. A method for producing a hybrid maize seed comprising crossing a first inbred parent maize plant with a second inbred parent maize plant and harvesting the resultant hybrid maize seed, wherein said first inbred parent maize plant or second said parent maize plant is the maize plant of claim 2.

11. A hybrid maize seed produced by the method of claim 10.

12. A maize plant, or a part thereof, produced by growing the seed of claim 11.

13. A method for producing a HMA699ND-derived maize plant, comprising:
    (a) crossing inbred maize line HMA699ND, representative seed of said line having been deposited under ATCC accession No. PTA-9428, with a second maize plant to yield progeny maize seed; and
    (b) growing said progeny maize seed, under plant growth conditions, to yield said HMA699ND-derived maize plant.

14. The method of claim 13, further comprising:
    (c) crossing said HMA699ND-derived maize plant with itself or another maize plant to yield additional HMA699ND-derived progeny maize seed;
    (d) growing said progeny seed of step (c) under plant growth conditions to yield additional HMA699ND-derived maize plants; and
    (e) repeating the crossing and growing steps of (c) and (d) from 0 to 7 times to generate further HMA699ND-derived maize plants.

15. A maize plant produced by the method of claim 13.

16. A method for producing a nutritionally enhanced hybrid maize seed comprising crossing a first inbred parent maize plant with a second inbred parent maize plant and harvesting the resultant hybrid maize seed, wherein said first inbred parent maize plant or second said parent maize plant is the maize plant of claim 2.

17. A hybrid maize seed produced by the method of claim 16.

18. A maize plant, or a part thereof, produced by growing the seed of claim 17.

19. The maize plant of claim 2 further comprising a transgene which confers tolerance or resistance to an herbicide.

20. The maize plant of claim 19 wherein the herbicide is selected from the group consisting of imidazolinone, sulfonylurea, glyphosate, glufosinate, triazine, and dicamba.

21. The maize plant of claim 2 further comprising a transgene that confers insect tolerance or resistance.

22. The maize plant of claim 21, wherein the transgene encodes a *Bacillus thuringiensis* endotoxin.

23. The maize plant of claim 2 further comprising a transgene that confers disease tolerance or resistance.

24. The maize plant of claim 2 further comprising a transgene encoding a phytase.

25. A method of introducing a desired trait into maize inbred line HMA699ND comprising:
(a) crossing HMA699ND plants grown from HMA699ND seed, representative seed of which has been deposited under ATCC Accession No. PTA-9428, with plants of another maize line that comprise a desired trait to produce $F_1$ progeny plants;
(b) selecting $F_1$ progeny plants that have the desired trait;
(c) crossing the selected progeny plants with the HMA699ND plants to produce backcross progeny plants;
(d) selecting for backcross progeny plants that have the desired trait and physiological and morphological characteristics of maize inbred line HMA699ND listed in Table 1 to produce selected backcross progeny plants; and
(e) repeating steps (c) and (d) one or more times in succession to produce selected backcross progeny plants that comprise the desired trait and substantially all of the physiological and morphological characteristics of maize inbred line HMA699ND listed in Table 1 when grown in the same environmental conditions.

26. A plant produced by the method of claim 25, wherein the plant has the desired trait and substantially all of the physiological and morphological characteristics of maize inbred line HMA699ND listed in Table 1 when grown in the same environmental conditions.

27. The plant of claim 26, wherein the desired trait is selected from the group consisting of stress tolerance, herbicide tolerance or resistance, insect tolerance or resistance, nematode tolerance or resistance, disease tolerance or resistance, and decreased phytate.

28. The plant of claim 26, wherein the desired trait is herbicide tolerance or resistance and the tolerance or resistance is conferred to an herbicide selected from the group consisting of imidazolinone, sulfonylurea, glyphosate, glufosinate, triazine, and dicamba.

29. The plant of claim 26, wherein the desired trait is insect tolerance or resistance and the insect tolerance or resistance is conferred by a transgene encoding a *Bacillus thuringiensis* endotoxin.

30. A maize plant, or a part thereof, having all of the physiological and morphological characteristics of maize inbred line HMA699ND, wherein a sample of the seed of maize inbred line HMA699ND was deposited under ATCC Accession NO. PTA-9428.

31. A method of producing a maize plant comprising the steps of:
(a) growing a progeny plant produced by crossing the plant of claim 30 with a second maize plant;
(b) crossing the progeny plant with itself or a different plant to produce a seed of progeny plant of a subsequent generation;
(c) growing a progeny plant of a subsequent generation from said seed and crossing the progeny plant of a subsequent generation with itself or a different plant; and
(d) repeating steps (b) and (c) for an additional 0-5 generation to produce a maize plant.

32. The method of claim 31 wherein the produced maize plant is an inbred maize plant.

33. The method of claim 32, further comprising the step of crossing the inbred maize plant with a second, distinct inbred maize plant to produce an F1 hybrid maize plant.

34. A method for developing a second maize plant in a maize plant breeding program comprising applying plant breeding techniques to a first maize plant, or parts thereof, wherein said first maize plant is the maize plant of claim 30, and wherein application of said techniques results in development of said second maize plant.

35. The method for developing a maize plant in a maize plant breeding program of claim 34 wherein plant breeding techniques are selected from the group consisting of recurrent selection, backcrossing, pedigree breeding, restriction length polymorphism enhanced selection, genetic marker enhanced selection, and transformation.

36. A method of plant breeding comprising the steps of:
(a) obtaining a molecular marker profile of maize inbred line HMA699ND, representative seed of said line having been deposited under ATCC Accession No. PTA-9428;
(b) obtaining an F1 hybrid seed for which the maize plant of claim 30 is a parent;
(c) crossing a plant grown from the F1 hybrid seed with a different maize plant; and
(d) selecting progeny that retain one or more markers of interest from the molecular marker profile of HMA699ND.

37. The maize plant of claim 2 further comprising a transgene.

* * * * *